United States Patent [19]  [11] 3,990,459
Papantoniou  [45] Nov. 9, 1976

[54] CATIONIC GRAFT AND CROSS-LINKED COPOLYMERS IN WAVESETTING LOTIONS

[75] Inventor: Christos Papantoniou, Epinay-sur-Seine, France

[73] Assignee: Societe Anonyme dite: L'Oreal, Paris, France

[22] Filed: June 19, 1973

[21] Appl. No.: 371,514

[30] Foreign Application Priority Data

June 20, 1972 Luxemburg .............................. 65552

[52] U.S. Cl. ................................. 132/7; 260/78.41; 260/895; 424/DIG. 2; 424/70; 424/71; 424/78; 424/81; 526/16; 526/30; 526/42; 526/263; 526/271; 526/312; 526/325; 526/332

[51] Int. Cl.² ..................... A45D 7/00; A61R 7/11
[58] Field of Search ................. 424/71, 78, 709, 81, 424/DIG. 1, DIG. 2; 260/78.4, 78.4 D, 78.4 E, 80.72, 80.73, 895; 132/7

[56] References Cited
UNITED STATES PATENTS

| | | | |
|---|---|---|---|
| 3,188,275 | 6/1965 | Erlemann | 424/71 |
| 3,405,084 | 10/1968 | Bohac et al. | 424/71 X |
| 3,423,367 | 1/1969 | Merijan et al. | 424/71 X |
| 3,546,321 | 12/1970 | Jabloner | 260/874 |
| 3,632,840 | 1/1972 | Vandenberg | 260/895 X |
| 3,634,368 | 1/1972 | Palmer | 260/80.72 |
| 3,743,715 | 7/1973 | Viout et al. | 424/47 |

*Primary Examiner*—V. D. Turner
*Assistant Examiner*—Vera C. Clarke
*Attorney, Agent, or Firm*—Mason, Mason, & Albright

[57] ABSTRACT

Cationic graft and cross-linked copolymers are provided which have excellent properties for use in cosmetic compositions, in particular wavesetting lotions. These copolymers are derived by copolymerizing:
    a. at least one cosmetic monomer;
    b. dimethylaminoethyl methacrylate;
    c. polyethylene glycol; and
    d. poly unsaturated polyunsaturated cross-linking agent.

5 Claims, No Drawings

CATIONIC GRAFT AND CROSS-LINKED COPOLYMERS IN WAVESETTING LOTIONS

The present invention relates to novel cationic,/graft and cross-linked copolymers.

It has already been proposed to use in cosmetic compositions such as hair lacquers and wavesetting lotions a variety of different types of homo- and co-polymers. Amongst these one can mention polyvinyl pyrrolidone, copolymers such as vinyl pyrrolidone/vinyl acetate copolymer, copolymers obtained from vinyl acetate and an unsaturated carboxylic acid such as crotonic acid, copolymers obtained from vinyl acetate, crotonic acid and an acrylic or methacrylic ester or an alkyl vinyl ether, copolymers obtained from vinyl acetate, crotonic acid and a vinyl ester of a long-chain acid or an allyl or methallyl ester of a long-chain acid, copolymers derived from an ester of an unsaturated alcohol and a short-chain saturated carboxylic acid, from a short-chain unsaturated acid and from an ester of a long-chain saturated alcohol and a short-chain unsaturated acid, and copolymers obtained by polymerizing at least one unsaturated ester and at least one unsaturated acid.

Some of these copolymers, which have been used to a very large extent, do possess good affinity for the keratin of the hair but, nevertheless, they do not possess the combination of properties which are required if excellent wavesetting lotions are to be obtained.

It has now been found, very surprisingly, according to the present invention, that it is possible to obtain excellent cosmetic compositions, in particular wavesetting lotions, using a certain type of copolymer which is, at the same time, cationic, grafted and cross-linked.

According to the present invention there is provided such a copolymer obtained by copolymerization of the following:
 a. at least one cosmetic monomer;
 b. dimethylaminoethyl methacrylate;
 c. polyethylene glycol; and
 d. a poly unsaturated cross-linking agent.

Compositions containing these novel copolymers give rise to better results than those available hitherto. Wavesetting lotions containing such copolymers form films having a lacquerability which is noticeably better than that obtained with the known resins. The copolymers of the present invention also provide other advantages. In particular, the films obtained possess a higher gloss than those obtained with the known copolymers. Furthermore, they possess a very great affinity for the hair so that they adhere better to the hair which enables the hair to be combed without significant loss of the copolymer film on the hair. It is, of course, well known that with the known hair lacquers and the like when one combs the hair effectively all of the resin becomes detached from the hair and falls in the form of a white powder. In contrast, with the compositions of the present invention it is possible to comb the hair without significant loss of the copolymer although the copolymer can readily be removed by brushing or washing with the aid of a conventional shampoo.

By the expression "graft and cross-linked copolymer" is meant a copolymer which contains a principal polymer chain possessing branches or grafts which are attached one to another with the aid of a cross-linking agent. Thus, in effect, the graft and cross-linked copolymers possess a network of branches, the density of which depends on the degree of unsaturation of the cross-linking agent.

Graft copolymers are, of course, well known and they can be represented schematically in the following manner:

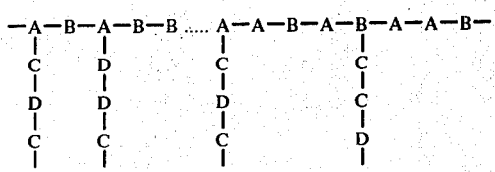

FIG. 1

The principal chain -A-B-A-B-B . . . A-A-B-A-B . . . represents the "backbone" of the graft copolymer while the chains -C-D . . . D-C- constitute the grafts. A graft and cross-linked copolymer can be represented schematically in the following manner:

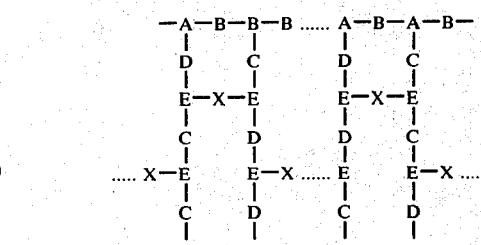

FIG. 2

The principal chain or the "backbone" -A-B-B-B . . . A-B-A-B- is identical to that in the graft copolymer as are the grafts. However, between these grafts and chains there are present the radicals -E-X-E- which are attached to different grafts and/or to different "backbones" of the polymer.

The radicals -E-X-E- are derived from the cross-linking agent which is doubly unsaturated as indicated in FIG. 2 thus giving rise to two-dimensional cross-linking. It will be appreciated, however, that the cross-linking agent can have a higher degree of unsaturation which gives rise to three-dimensional structures.

The cross-linking agent used in the present invention is preferably ethylene glycol dimethacrylate, a diallyl phthalate, a divinyl benzene, tetraallyloxyethane or a polyallyl sucrose having 2 to 5 allyl groups per mol of sucrose. The degree of unsaturation in the cross-linking agents is thus from 2, to 5 in the case of the polyallyl sucroses.

The term "cosmetic monomer" refers to a monomer which has been used in the past to prepare a polymer having utility in the cosmetics field. A variety of different types of monomer can be used including, for example, a vinyl ester of an acid having 2 to 18 carbon atoms, an allyl or methallyl ester of an acid having 2 to 18 carbon atoms, an acrylate or methacrylate of a saturated alcohol having 1 to 18 carbon atoms, an alkyl vinyl ether in which the alkyl radical has 2 to 18 carbon atoms, an olefin having 4 to 18 carbon atoms, a vinyl heterocycle, a di-alkyl or N,N'-dialkylaminoalkyl maleate in which each alkyl radical has 1 to 3 carbon atoms, or an anhydride of an unsaturated acid. Preferred such monomers include:

vinyl acetate
vinyl propionate
methyl methacrylate
stearyl methacrylate
lauryl methacrylate
ethyl vinyl ether
cetyl vinyl ether
stearyl vinyl ether
hexene-1
octadecene
N-vinyl pyrrolidone
N,N-diethylaminoethyl monomaleate
diethyl maleate and
maleic anhydride.

The polyethylene glycol onto which the grafting takes place suitably has a molecular weight between 200 and several million, preferably between 300 and 30,000.

The copolymers of the present invention are preferably derived from:

a. 3 to 95% by weight of at least one cosmetic monomer;
b. 3 to 95% by weight of dimethylaminoethyl methacrylate;
c. 2 to 50% by weight, preferably 5 to 30% by weight, of polyethylene glycol; and
d. 0.01 to 8% by weight, based on the total weight of (a) + (b) + (c), of the specified cross-linking agent.

Thus if one copolymerizes 123 grams (41%) of vinyl acetate, 147 grams (49%) of dimethylaminoethyl methacrylate and 30 grams (10%) of polyethylene glycol the amount of cross-linking agent required is between 0.03 grams (0.01%) and 24 grams (8%).

The graft and cross-linked copolymers of the present invention can be in the form of their quaternary salts. This is because the dimethylaminoethyl methacrylate can be quaternized. This can be carried out before or after the copolymer has been obtained. Suitable quaternizing agents include dialkyl sulphates, for example diethyl sulphate and dimethyl sulphate, benzyl halides, for example benzyl chloride, bromide or iodide, and alkyl halides as well as the other known quaternizing agents.

The copolymers of the present invention generally have a molecular weight of between 10,000 and one million, preferably between 15,000 and 500,000.

According to the present invention, the copolymers of the present invention can be obtained by polymerization in a conventional manner, for example in bulk, in suspension, as an emulsion or in solution in a solvent. However, the polymerization is preferably carried out in bulk or in suspension.

The conventional free radical initiation polymerization catalysts can be used, the particular one depending on the reactants involved. Typical of such initiators include peroxides such as benzoyl peroxide, lauryl peroxide, acetyl peroxide and benzoyl hydroperoxide, catalysts which, on decomposition, produce an inert gas such as azo bis-isobutyronitrile and redox catalysts such as sodium persulphate, sodium sulphite and hydrogen peroxide. The concentration of initiator is generally between 0.2 and 15%, preferably 0.5 to 12%, by weight based on the total weight of the reactants i.e. cosmetic monomer, dimethylaminoethyl methacrylate, polyethylene glycol and cross-linking agent.

If the polymerization is carried out in suspension, the various reactants should be immiscible with water or the inert liquid used as the continuous phase. In consequence, if one uses water as the continuous phase, it is necessary to saturate this with a mineral salt such as sodium chloride because polyethylene glycol is soluble in water. If one or more of the cosmetic monomers is also soluble in water the addition of sodium chloride also has the effect of putting this in suspension so that all the reactants are present in the form of droplets or globules.

Conventional suspending agents can be used to facilitate the reaction such as hydroxyethyl cellulose known under the trade name "CELLOSIZE," cross-linked polyacrylic acid known under the trade name "CARBOPOL" and the polyvinyl alcohols known under the trade name "RHODO VIOL."

If the polymerization is carried out in an emulsion, an emulsifying agent such as potassium stearate, potassium palmitate, potassium laurate or laurylamine hydrochloride can be used.

The molecular weight of the graft and cross-linked copolymer can be regulated by introducing during the polymerization small quantities (suitably from 0.05 to 0.4% by weight) of a chain regulator such as an aldehyde such as butyraldehyde, halogenated substances such as chloroform, bromoform and carbon tetrachloride and mercaptans such as lauryl mercaptan.

The present invention also provides a composition suitable for use in cosmetics which comprises at least one of the novel copolymers together with an appropriate vehicle. Such cosmetic compositions are suitably in the form of wavesetting lotions. Such lotions are generally aqueous or aqueous-alcoholic solutions containing 5 to 70% of alcohol, the concentration of the copolymer generally being between 0.4 and 5% by weight. The alcohols generally used in such lotions are preferably low molecular weight aliphatic alcohols (i.e., of 1 to 6, suitably of 1 to 4, carbon atoms) such as ethanol and isopropanol.

The aqueous solutions of the present invention can also be used to treat the hair so as to brighten it making it more lively and to facilitate disentangling. In this case, the aqueous solutions are preferably applied after rinsing and optionally after shampooing. The composition is allowed to act on the hair for several minutes, for example 5 to 10 minutes, and then the hair is rinsed with water.

It is to be understood that all the ingredients conventionally used in such cosmetic compositions can be present in the compositions of the present invention such as plasticizing agents, perfumes and hair dyes.

The present invention also provides a process for wavesetting hair which comprises impregnating the hair with a lotion of the present invention, winding the hair on wavesetting rollers (generally having a diameter from 15 to 30 mm) and then drying the hair on the rollers.

The following Examples further illustrate the present invention.

EXAMPLE 1

200 grams of an aqueous solution containing 52 grams of sodium chloride and 0.3 grams of "Cellosize" are introduced into a 1 liter flask equipped with a mechanical stirrer, a nitrogen inlet tube, a thermometer and a condenser. Then a solution containing 41.8 grams of methyl methacrylate, 48.2 grams of dimethylaminoethyl methacrylate (MADAME), 10 grams of polyethylene glycol (molecular weight (MW) 20,000), 0.8 grams of ethylene glycol dimethacrylate and 2 grams of azo bis-isobutyronitrile is added. The mixture is then heated with agitation to 75° C. for 3 hours. After this time the polymerization is terminated. Beads are obtained which are then washed and recovered in the usual manner. Yield: 90%.

QUATERNIZATION OF THIS POLYMER 20 grams of the graft and cross-linked polymer obtained are dissolved in 200 grams of absolute ethanol. The mixture is refluxed and then 7.7 grams of dimethyl sulphate added with agitation. After heating to 80° C., with stirring, for 14 hours, the quaternized polymer has precipitated in the reaction mixture. By adding 50 grams of water a clear solution is obtained. The polymer is purified by precipitation in dioxane. Viscosity (as a 5% by weight solution in dimethyl formamide at 35° C): 40 centipoises.

EXAMPLE 2

Following the procedure of Example 1 the following materials are polymerized:

| | |
|---|---|
| N-vinyl pyrrolidone | 62 g |
| MADAME | 28 g |
| Polyethylene glycol MW 20,000 | 10 g |
| Tetraallyloxyethane | 0.02 g |
| Azo bis-isobutyronitrile | 4 g |
| Sodium chloride | 152 g |
| 0.06% by weight solution of "Cellosize" in water | 400 g |

The polymer obtained is quaternized with 22.5 grams of dimethyl sulphate. This polymer has a viscosity (measured as before) of 7 centipoises.

EXAMPLE 3

25 grams of methyl methacrylate, 27 grams of stearyl methacrylate, 38 grams of N,N-dimethylaminoethyl methacrylate, 10 grams of polyethylene glycol of molecular weight 20,000, 0.1 gram of ethylene glycol dimethacrylate and 1.5 grams of azo bis-isobutyronitrile are introduced into a 1 liter flask equipped with a mechanical stirrer, a nitrogen inlet tube and a condenser. The mixture is heated at 80° C. for 8 hours.

After cooling 500 grams of absolute ethanol are introduced. The mixture is heated again until the polymer is completely dissolved in the ethanol. The N,N-dimethylaminoethyl methacrylate is quaternized by introducing 30.5 grams of dimethyl sulphate and then heating for a further 4 hours at 80° C. The resulting copolymer has a viscosity of 3.8 centipoises (measured as a 2% by weight solution in a 50:50 aqueous ethanolic solution at 34.6° C.).

EXAMPLE 4

Proceeding as in Example 3, the following materials are polymerized:

| | |
|---|---|
| Ethyl vinyl ethyl | 20 g |
| MADAME | 35 g |
| N-vinyl pyrrolidone | 35 g |
| Polyethylene glycol MW 20,000 | 10 g |
| Azo bis-isobutyronitrile | 3 g |

This polymer is quaternized with 28 grams of dimethyl sulphate. The polymer obtained has a viscosity of 27 centipoises (as a 2% by weight solution in a 50:50 aqueous ethanolic solution at 34.6° C.).

EXAMPLE 5

Following the procedure of Example 3, the following materials are polymerized:

| | |
|---|---|
| N-vinyl pyrrolidone | 56 g |
| MADAME | 24 g |
| N,N'-diethylaminoethyl monomaleate | 10 g |
| Polyethylene glycol MW 20,000 | 10 g |
| Tetraallyloxyethane | 0.1 g |
| Azo bis-isobutyronitrile | 1.5 g |

The polymer is then quaternized with 30 grams of dimethyl sulphate. The resulting copolymer has a viscosity of 2.40 centipoises (measured as a 2% by weight solution in a 50:50 aqueous ethanolic solution at 34.6° C.).

EXAMPLE 6

Following the procedure of Example 3, the following materials are polymerized:

| | |
|---|---|
| Methyl methacrylate | 25 g |
| Lauryl methacrylate | 27 g |
| MADAME | 38 g |
| Polyethylene glycol MW 20,000 | 10 g |
| Ethylene glycol dimethacrylate | 0.1g |
| Azo bis-isobutyronitrile | 1.5g |

This polymer is quaternized with 30.5 grams of dimethyl sulphate. The resulting polymer has a viscosity of 2.55 centipoises (measured as a 2% by weight solution in a 50:50 aqueous ethanolic solution at 34.6° C.).

EXAMPLE 7

Following the procedure of Example 3, the following ingredients are polymerized:

| | |
|---|---|
| Vinyl propionate | 45 g |
| MADAME | 45 g |
| Polyethylene glycol MW 20,000 | 10 g |
| Tetraallyloxyethane | 0.2 g |
| Azo bis-isobutyronitrile | 1.5 g |

This polymer is quaternized with 36 grams of dimethyl sulphate. It possesses a viscosity of 3 centipoises (measured as a 2% by weight solution in a 50:50 aqueous ethanolic solution at 34.6° C.).

EXAMPLE 8

Following the procedure of Example 3, the following ingredients are polymerized:

| | |
|---|---|
| Ethyl vinyl ether | 20 g |
| MADAME | 70 g |
| Polyethylene glycol MW 20,000 | 10 g |
| Tetraallyloxyethane | 0.2 g |
| Azo bis-isobutyronitrile | 1.5 g |

This polymer is quaternized with 56 grams of dimethyl sulphate. The polymer obtained possesses a viscosity of 7.7 centipoises (measured as a 2% by weight solution in a 50:50 aqueous ethanolic solution at 34.6°C.).

EXAMPLE 9

Following the procedure of Example 3, the following are polymerized:

| | |
|---|---|
| Octadecene-1 | 15 g |
| MADAME | 75 g |
| Polyethylene glycol MW 20,000 | 10 g |
| Ethylene glycol dimethacrylate | 0.1 g |
| Azo bis-isobutyronitrile | 1.5 g |

This polymer is quaternized with 60 grams of dimethyl sulphate. The resulting polymer possesses a viscosity of 2.77 centipoises (measured as a 2% by weight solution in 50:50 aqueous ethanolic solution at 34.6° C.).

EXAMPLE 10

Following the procedure of Example 3, the following ingredients are polymerized:

| | |
|---|---|
| Vinyl acetate | 41 g |
| MADAME | 49 g |
| Polyethylene glycol MW 20,000 | 10 g |
| Tetraallyloxyethane | 0.2 g |
| Azo bis-isobutyronitrile | 1.5 g |

This polymer is quaternized with 39 grams of dimethyl sulphate. Viscosity (measured as in Example 9) : 3.55 centipoises.

EXAMPLE 11

Following the procedure of Example 3, the following ingredients are polymerized:

| | |
|---|---|
| Methyl methacrylate | 30 g |
| MADAME | 63 g |
| Polyethylene glycol MW 20,000 | 7 g |
| Ethylene glycol dimethacrylate | 0.08 g |
| Azo bis-isobutyronitrile | 1.5 g |

This polymer is quaternized with 50.4 grams of dimethyl sulphate. The polymer obtained possesses a viscosity of 3.6 centipoises (measured as a 2% by weight solution in a 50:50 aqueous ethanolic solution at 34.6° C.).

EXAMPLE 12

Following the procedure of Example 3, the following ingredients are polymerized:

| | |
|---|---|
| Vinyl acetate | 10 g |
| N-vinyl pyrrolidone | 56 g |
| MADAME | 24 g |
| Polyethylene glycol MW 20,000 | 10 g |
| Tetraallyloxyethane | 0.02 g |
| Azo bis-isobutyronitrile | 1.5 g |

This polymer is quaternized with 19.2 grams of dimethyl sulphate. The polymer obtained possesses a viscosity of 3.6 centipoises (measured as a 2% by weight solution in a 50:50 aqueous ethanolic solution at 34.6° C.).

EXAMPLE 13

Following the procedure of Example 3, the following ingredients are polymerized:

| | |
|---|---|
| N-vinyl pyrrolidone | 54 g |
| Diethyl maleate | 18 g |
| MADAME | 18 g |
| Polyethylene glycol MW 20,000 | 10 g |
| Tetraallyloxyethane | 0.02 g |
| Azo bis-isobutyronitrile | 1.5 g |

This polymer is quaternized with 14.4 grams of dimethyl sulphate. The polymer obtained possesses a viscosity of 3.2 centipoises (measured as a 2% by weight solution in a 50:50 aqueous ethanolic solution at 34.6° C).

EXAMPLE 14

Following the procedure of Example 3, the following ingredients are polymerized:

| | |
|---|---|
| Vinyl acetate | 20 g |
| N-vinyl pyrrolidone | 42 g |
| Diethyl maleate | 14 g |
| MADAME | 14 g |
| Polyethylene glycol MW 20,000 | 10 g |
| Tetraallyloxyethane | 0.02 g |
| Azo bis-isobutyronitrile | 1.5 g |

This polymer is quaternized with 11.2 grams of dimethyl sulphate. The polymer obtained possesses a viscosity of 4.3 centipoises (measured as a 2% by weight solution in a 50:50 aqueous ethanolic solution at 34.6° C.).

EXAMPLE 15

Following the procedure of Example 3, the following ingredients are polymerized:

| | |
|---|---|
| N-vinyl pyrrolidone | 54 g |
| Maleic anhydride | 18 g |
| MADAME equaternized with dimethyl sulphate | 18 g |
| Polyethylene glycol MW 20,000 | 10 g |
| Tetraallyloxyethane | 0.02 g |
| Azo bis-isobutyronitrile | 1.5 g |

The polymer obtained possesses a viscosity of 3.7 centipoises (measured as a 2% by weight solution in a 50:50 aqueous ethanolic solution at 34.6° C.).

EXAMPLE 16

Following the procedure of Example 3, the following ingredients are polymerized:

| | |
|---|---|
| N-vinyl pyrrolidone | 55 g |
| MADAME | 35 g |
| Polyethylene glycol MW 4,000 | 10 g |
| Tetraallyloxyethane | 0.02 g |
| Azo bis-isobutyronitrile | 1.5 g |

This polymer is quaternized with 28 grams of dimethyl sulphate. The polymer obtained possesses a viscosity of 6.4 centipoises (measured as a 2% by weight solution in a 50:50 aqueous ethanolic solution at 34.6° C.).

EXAMPLE 17

Following the procedure of Example 3, the following ingredients are polymerized:

| | |
|---|---|
| N-vinyl pyrrolidone | 66 g |
| MADAME | 24 g |
| Polyethylene glycol MW 1,500 | 10 g |
| Tetraallyloxyethane | 0.02 g |
| Azo bis-isobutyronitrile | 1.5 g |

This polymer is quaternized with 19.2 grams of dimethyl sulphate. The polymer obtained possesses a viscosity of 5.1 centipoises (measured as a 2% by weight solution in a 50:50 aqueous ethanolic solution at 34.6° C.).

EXAMPLE A

A wavesetting lotion is prepared by mixing the following ingredients:

| | |
|---|---|
| Polymer prepared according to Example 1 | 2 g |
| Perfume | 0.1 g |
| Ethyl alcohol | 45 g |
| Water q.s.p. | 100 g |

This wavesetting lotion is applied in a conventional manner to the hair to which it gives a brilliant appearance; it adheres well to the hair.

The polymer of Example 1 can be replaced by the same quantity of the polymer prepared in any one of Examples 2, 6, 8 and 12, with similar results.

EXAMPLE B

A wavesetting lotion is prepared by mixing the following ingredients:

| | |
|---|---|
| Polymer prepared according to Example 5 | 3.5 g |
| Perfume | 0.1 g |
| Dyestuff sufficient to colour the lotion | 0.2 g |
| Isopropyl alcohol | 40 g |
| Water q.s.p. | 100 g |

In this Example, the polymer of Example 5 can be replaced by the same quantity of the polymer prepared in any one of Examples 3, 7, 10 and 13 with similar results.

After impregnation of hair with one of these lotions, the hair is rolled on wavesetting rollers having a diameter of 15 to 30 mm and then dried on the rollers with the application of heat. After removing the rollers, an excellent set with a good hold is obtained.

EXAMPLE C

A wavesetting lotion is prepared by mixing the following ingredients:

| | |
|---|---|
| Polymer prepared according to Example 4 | 1.5 g |
| Perfume | 0.1 g |
| Ethyl alcohol | 45 g |
| Water q.s.p. | 100 g |

In this Example the polymer of Example 4 can be replaced by the same quantity of the polymer prepared according to any one of Examples 8, 12 and 15, with similar results.

EXAMPLE D

A wavesetting lotion is prepared by mixing the following ingredients:

| | |
|---|---|
| Polymer prepared according to Example 6 | 2 g |
| 2-Amino-2-methyl-propanol q.s.p. pH = | 7 |
| Isopropyl alcohol | 40 g |
| Water q.s.p. | 100 g |

In this Example the polymer of Example 6 can be replaced by the same quantity of one of the polymers prepared in any one of Examples 8 to 11, with similar results.

EXAMPLE E

A wavesetting lotion is prepared by mixing the following ingredients:

| | |
|---|---|
| Polymer prepared according to Example 5 | 3 g |
| 2-Amino-2-methyl-propan-1,3-diol q.s.p. pH = | 7.2 |
| Perfume | 0.1 g |
| Ethyl alcohol | 45 g |
| Water q.s.p. | 100 g |

This wavesetting lotion is applied in a conventional manner to the hair. It gives to the hair an excellent hold with a glossy appearance without making it at all sticky.

In this Example the polymers of Example 5 can be replaced by the same quantity of one of the polymers prepared in Examples 16 and 17, with similar results.

EXAMPLE F

A hair treatment composition is prepared by mixing the following ingredients:

| | |
|---|---|
| Polymer prepared according to Example 2 | 1 g |
| Perfume | 0.1 g |
| Water q.s.p. | 100 g |

This composition is applied for several minutes to hair which has previously been shampooed and rinsed with water. After further rinsing with water, brilliant and supple hair is obtained which disentangles very easily.

Similar results are obtained when the copolymer of Example 2 is replaced by the same quantity of one of the polymers prepared in any one of Examples 5, 12, 13, 16 and 17.

EXAMPLE G

A treatment composition for the hair is prepared by mixing the following ingredients:

| | |
|---|---|
| Polymer prepared according to Example 4 | 2.5 g |
| Perfume | 0.2 g |
| Water q.s.p. | 100 g |

By proceeding as in Example F brilliant and supple hair which disentangles very easily is obtained.

In this Example, the polymer of Example 4 can be replaced by the same quantity of the polymer prepared according to Example 1 or 8, with similar results.

I claim:

1. A cosmetic composition comprising in a solvent selected from the group consisting of water, an aliphatic alcohol having 1 to 6 carbon atoms and an aqueous-alcoholic solution of said alcohol, 0.4 to 5 % weight of a cationic graft cross linked copolymer of:
   a. 3 to 95 % by weight of at least one monomer selected from the group consisting of: vinyl acetate, vinyl propionate, methyl methacrylate, stearyl methacrylate, lauryl methacrylate, ethyl vinyl ether, cetyl vinyl ether, stearyl vinyl ether, hexene-1, octadecene, N-vinyl pyrrolidone, N,N-diethylaminoethyl monomaleate, diethyl maleate and maleic anhydride;
   b. 3 to 95 % by weight of dimethylaminoethyl methacrylate;
   c. 2 to 50 % by weight of polyethylene glycol having a molecular weight between 300 and 30,000;
   and d. 0.01 to 8 % by weight, based on the total weight of (a) + (b) + (c) of a cross-linking agent selected from the group consisting of: ethylene glycol dimethacrylate and tetraallyloxyethane; said copolymer having a molecular weight between 10,000 and 1,000,000.

2. The composition of claim 1, wherein said aqueous-alcoholic solution contains 5 to 70 % by weight of an aliphatic alcohol having 1 to 6 carbon atoms.

3. The composition of claim 1, wherein the copolymer is quaternized by a quaternizing agent selected from the group consisting of: dimethyl sulphate, diethyl sulphate, benzyl chloride, benzyl bromide and benzyl iodide.

4. The composition of claim 1, wherein said copolymer consists of about 62% N-vinyl pyrrolidone, 28% dimethylaminoethyl methacrylate, 10% polyethylene glycol and 0.02% tetraallyloxyethane.

5. A method of setting hair which comprises applying to the hair an effective amount of the composition claimed in claim 1, winding the hair on wavesetting rollers and drying the hair.

* * * * *